(12) United States Patent
Utsunomiya

(10) Patent No.: US 8,546,777 B2
(45) Date of Patent: Oct. 1, 2013

(54) RADIOGRAPHIC IMAGE CAPTURING DEVICE

(75) Inventor: Daisuke Utsunomiya, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 286 days.

(21) Appl. No.: 13/008,926

(22) Filed: Jan. 19, 2011

(65) Prior Publication Data

US 2011/0222663 A1 Sep. 15, 2011

(30) Foreign Application Priority Data

Mar. 12, 2010 (JP) .................................. 2010-056181

(51) Int. Cl.
*G01N 23/04* (2006.01)
(52) U.S. Cl.
USPC ........................................................ 250/580
(58) Field of Classification Search
USPC ........................................................ 250/580
See application file for complete search history.

(56) References Cited

U.S. PATENT DOCUMENTS

2011/0147601 A1* 6/2011 Niekawa et al. ......... 250/370.09

FOREIGN PATENT DOCUMENTS

| JP | 2004-180931 A | 7/2004 |
| JP | 2008-017021 A | 1/2008 |
| JP | 2009-050689 A | 3/2009 |
| WO | WO 2010021165 A1 * | 2/2010 |

OTHER PUBLICATIONS

Partial English language translation of the following: Office action dated Jul. 16, 2013 from the Japanese Patent Office in a Japanese patent application corresponding to the instant patent application. This office action translation is submitted now in order to supplement the understanding of patent document JP 2004-180931 which is cited in the office action and is being disclosed in the instant Information Disclosure Statement.

\* cited by examiner

*Primary Examiner* — David Porta
*Assistant Examiner* — Kenneth J Malkowski
(74) *Attorney, Agent, or Firm* — SOLARIS Intellectual Property Group, PLLC

(57) ABSTRACT

A radiographic image capturing device includes: a radiation detector that has plural sensor portions; a detection circuit that reads out, as electrical signals, electric charge quantities stored in each of the sensor portions and converts the electrical signals into digital image data; a receiver that receives electrical power; a power source that is charged by the electrical power and supplies electrical power for driving to at least the radiation detector and the detection circuit; and a controller which, in the case of performing video imaging, controls the detection circuit so as to allow electric charges to be stored in a predetermined storage period and which performs control such that, in the storage period of each imaging, it stops at least one of the charging of the power source with the received electrical power or the reception of the electrical power from the outside by the receiver.

5 Claims, 7 Drawing Sheets

RADIOGRAPHIC IMAGE CAPTURING DEVICE

CROSS-REFERENCE TO RELATED APPLICATION

This application is based on and claims priority under 35 USC 119 from Japanese Patent Application No. 2010-056181 filed on Mar. 12, 2010, which is incorporated by reference herein.

BACKGROUND

1. Technical Field

The present invention relates to a radiographic image capturing device.

2. Related Art

In recent years, radiation detectors such as flat panel detectors (FPD) that comprise a radiation-sensitive layer placed on a thin-film transistor (TFT) active matrix substrate, detect radiation such as X-rays with which the radiation detector has been irradiated, and output electrical signals representing a radiographic image expressed by the detected radiation have been put to practical use. These radiation detectors have advantages in that, as compared to conventional imaging plates, images can be checked instantaneously and videos can also be checked. As systems of converting radiation in radiation detectors, there are an indirect conversion system, in which a scintillator is used to convert the radiation into light and then a semiconductor layer such as a photodiode is used to convert the light into electric charges, and a direct conversion system, in which a semiconductor layer such as amorphous selenium is used to convert the radiation into electric charges; in each system, there exist various materials that can be used for the semiconductor layer.

Portable radiographic imaging devices (also called "electronic cassettes" below) into which such radiation detectors are built and which store radiographic image data outputted from the radiation detector have also been put to practical use.

Incidentally, fluoroscopy, in which video imaging is performed, consumes a lot of electrical power because the imaging operation is repeated continuously. For this reason, there is a wired connection type of electronic cassette that is used by connecting the electronic cassette via a cable to a control-use terminal (a so-called console) for performing stable electrical power supply or data transfer.

However, with the wired connection type of electronic cassette, there are cases where various types of noise are transmitted via the cable and the noise ends up rising on the image data.

Thus, in Japanese Patent Application Laid-Open (JP-A) No. 2008-17021, there is described a technology where, in a radiographic image capturing system having a wireless power feed device, wireless power feeding is prohibited at the time of imaging.

Further, in JP-A No. 2009-50689, there is a technology where, in regard to a radiographic image capturing system having a wireless communication device, imaging and wireless communication are not performed at the same time and supply of electrical power supply from an outside power source is shut off by wireless communication to eliminate the influence of power source noise.

It is conceivable to utilize the technologies described in JP-A No. 2008-17021 and JP-A No. 2009-50689 to house a built-in battery in the electronic cassette, shut off supply of electrical power via the cable at the time of fluoroscopy, and perform supply of electrical power from the built-in battery. However, as mentioned above, fluoroscopy consumes a lot of electrical power, so in a case where supply of electrical power via a communication cable is shut off at the time of imaging and supply of electrical power is performed from a built-in battery, the period in which a video can be captured is short.

SUMMARY

The present invention has been made in view of the circumstances described above, and it is an object thereof to provide a radiographic image capturing device that enables prolonged capture of a video while suppressing the effect of noise transmitted from an outside power source on radiographic images.

A radiographic image capturing device pertaining to one aspect of the present invention includes: a radiation detector that has plural sensor portions in which electric charges are generated as a result of being irradiated with radiation and which store the generated electric charges; a detection circuit that reads out, as electrical signals, electric charge quantities stored in each of the sensor portions of the radiation detector, converts the electrical signals it has read out into digital data, and detects image data representing a radiographic image; a receiver that receives external electrical power; a power source that is charged by the electrical power received by the receiver and that supplies electrical power for driving at least the radiation detector and the detection circuit; and a controller which, in the case of performing video imaging in which imaging is performed continuously, controls the detection circuit so as to allow electric charges to be stored in a predetermined storage period in each of the sensor portions of the radiation detector in each imaging and thereafter to read out the stored electric charges, and which performs control such that, in the storage period of each imaging, the controller stops at least one of the charging of the power source with the electrical power received by the receiver or the reception of the electrical power from the outside by the receiver, and performs control such that, in periods between the storage period of each imaging, it charges the power source with the electrical power received by the receiver.

BRIEF DESCRIPTION OF THE DRAWINGS

An exemplary embodiment of the present invention will be described in detail based on the following figures, wherein.

DETAILED DESCRIPTION

A mode for implementing the present invention will be described in detail below with reference to the drawings. Here, an example of a case where the present invention is applied to a radiology information system, which is a system that collectively manages information handled in a radiology department in a hospital, will be described.

Figure 1:
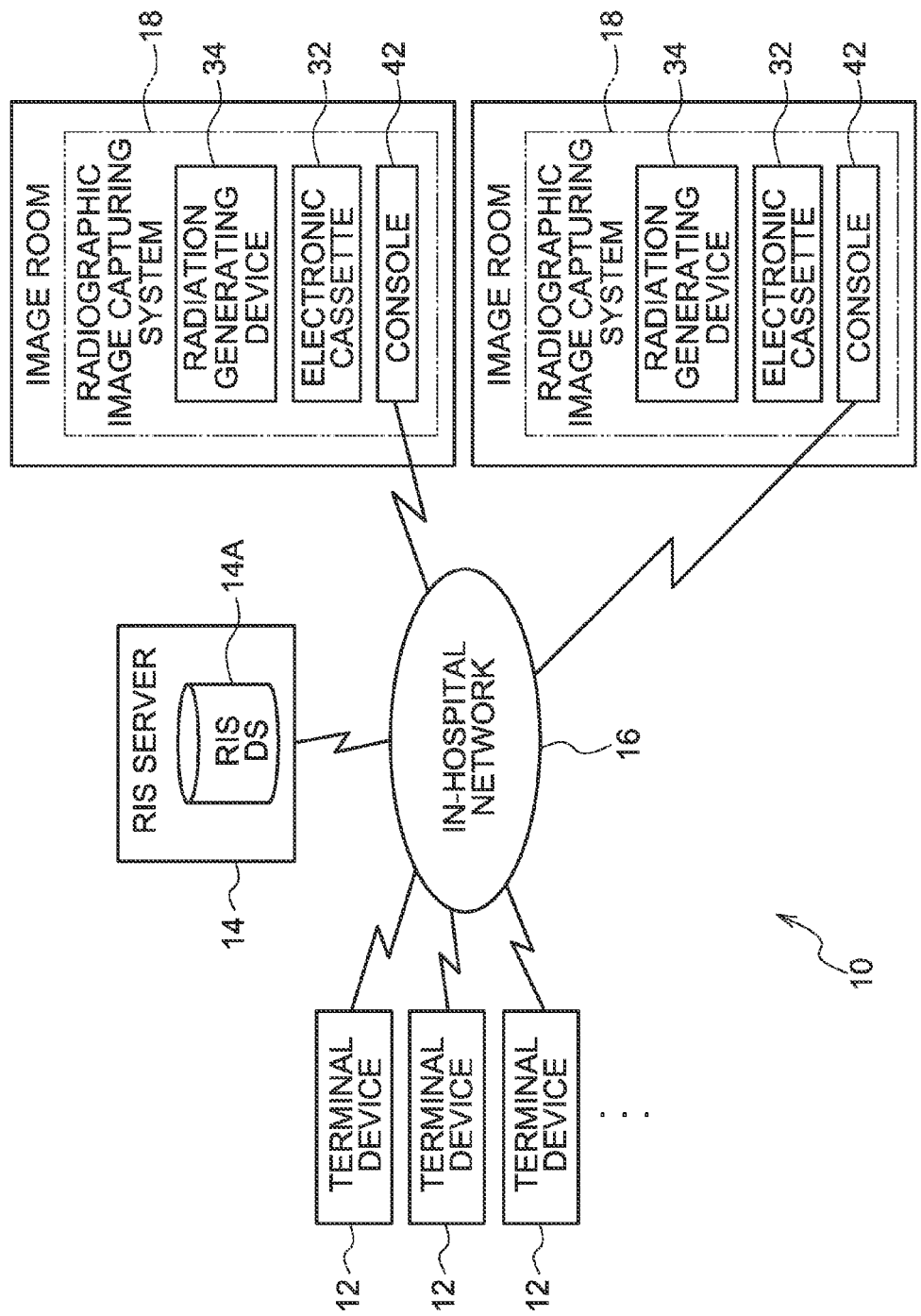
FIG. 1 is a block diagram showing the configuration of a radiology information system pertaining to the exemplary embodiment.

First, the configuration of a radiology information system (RIS) 10 (hereinafter called "the RIS 10") pertaining to the present exemplary embodiment will be described with reference to FIG. 1.

The RIS 10 is a system for managing information such as medical service appointments and diagnostic records in a radiology department and configures part of a hospital information system (hereinafter called "the HIS").

The RIS 10 has plural imaging request terminal devices 12 (hereinafter called "the terminal device(s) 12"), an RIS server 14, and radiographic image capturing systems 18 (hereinafter called "the imaging system(s) 18"). The imaging systems 18 are installed in individual radiographic imaging rooms (or operating rooms) in a hospital. The RIS 10 is configured as a result of the terminal devices 12, the RIS server 14, and the imaging systems 18 being connected to an in-hospital network 16 having a wired or wireless local area network (LAN). The RIS 10 configures part of the HIS disposed in the same hospital, and an HIS server (not shown) that manages the entire HIS is also connected to the in-hospital network 16.

The terminal devices 12 are devices for a doctor or a radiologic technologist to input and peruse diagnostic information and facility reservations. Radiographic image imaging requests and imaging reservations are also made via these terminal devices 12. Each of the terminal devices 12 is configured to include a personal computer having a display device, and the terminal devices 12 can communicate with each other via the RIS server 14 and the in-hospital network 16.

The RIS server 14 receives imaging requests from each of the terminal devices 12 and manages radiographic image imaging schedules in the imaging systems 18. The RIS server 14 is configured to include a database 14A.

The database 14A includes data relating to patients, such as attribute information of patients (names, sexes, dates of birth, ages, blood types, body weights, patient IDs, etc.), medical histories, consultation histories, and radiographic images captured in the past.

The imaging systems 18 capture radiographic images as a result of being operated by a doctor or a radiologic technologist in response to an instruction from the RIS server 14. Each of the imaging systems 18 is equipped with a radiation generating device 34, an electronic cassette 32, and a console 42. The radiation generating device 34 irradiates an examinee with a dose of radiation X (see FIG. 3) following exposure conditions from a radiation source 130 (see FIG. 2). The electronic cassette 32 has a built-in radiation detector 60 (see FIG. 3) that absorbs the radiation X that has passed through an imaging target site of a patient, generates electric charges, and produces image data representing a radiographic image on the basis of the generated electric charge quantity. The console 42 controls the electronic cassette 32 and the radiation generating device 34.

Figure 2:
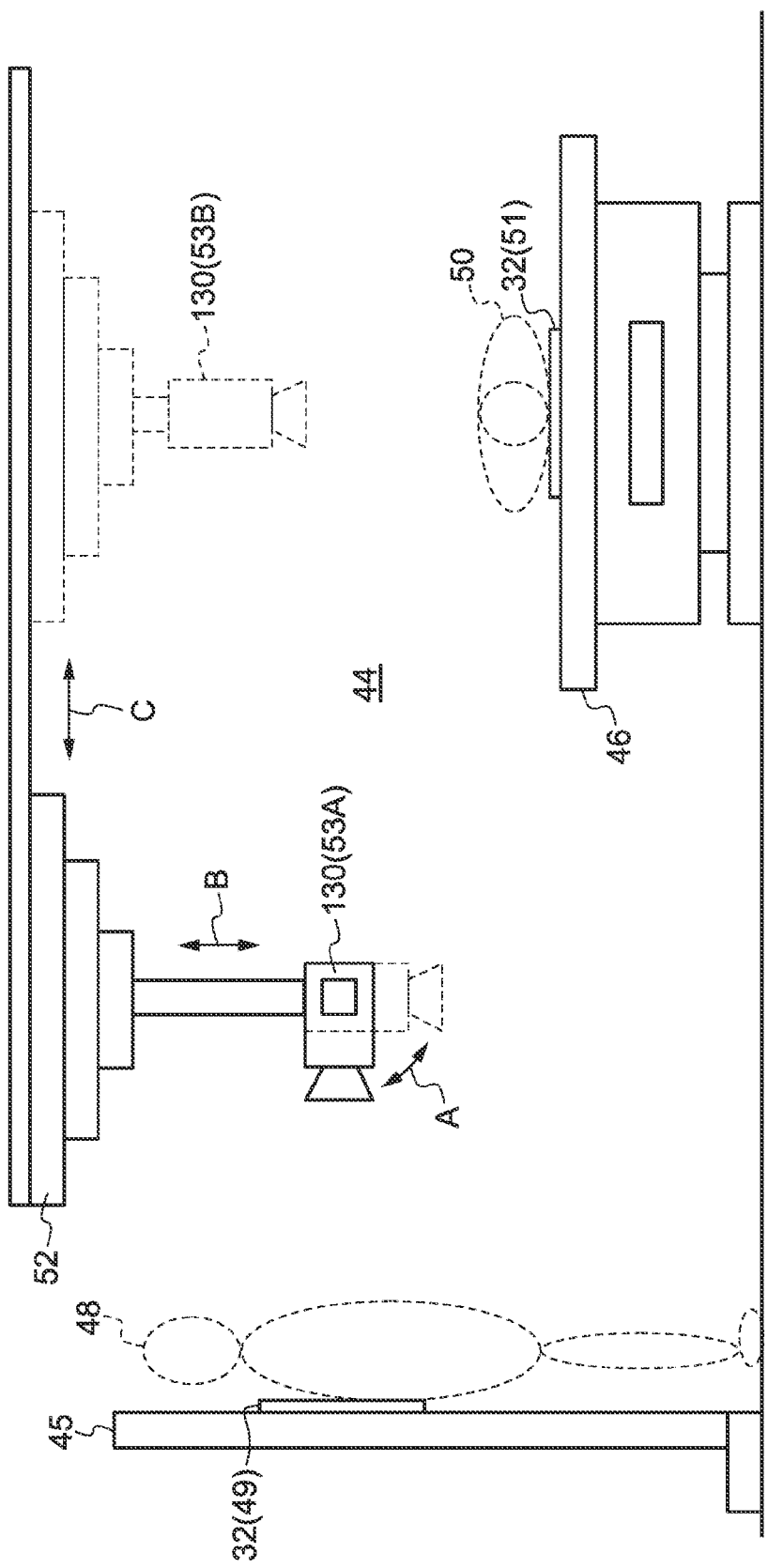
FIG. 2 is a diagram showing an operating room in which a radiographic image capturing system pertaining to the exemplary embodiment is installed.

FIG. 2 shows one example of the arrangement of the imaging system 18 pertaining to the present exemplary embodiment in a radiographic imaging room 44.

As shown in FIG. 2, a rack 45 and a bed 46 are installed in the radiographic imaging room 44. The rack 45 is for holding the electronic cassette 32 when performing radiographic imaging on a patient in a standing position. The bed 46 is for the patient to lie on when performing radiographic imaging on a patient in a lying position. The space in front of the rack 45 serves as an imaging position 48 of the patient when performing radiographic imaging on a patient in the standing position. The space above the bed 46 serves as an imaging position 50 of the patient when performing radiographic imaging on a patient in the lying position.

A supporting-and-moving mechanism 52 is also disposed in the radiographic imaging room 44. The supporting-and-moving mechanism 52 supports the radiation source 130 such that the radiation source 130 is rotatable about a horizontal axis (the direction of arrow A in FIG. 2), is movable in the vertical direction (the direction of arrow B in FIG. 2), and is movable in the horizontal direction (the direction of arrow C in FIG. 2) to enable both radiographic imaging of a patient in the standing position and radiographic imaging of a patient in the lying position using radiation from the single radiation source 130. Here, the supporting-and-moving mechanism 52 is equipped with a drive source that rotates the radiation source 130 about the horizontal axis, a drive source that moves the radiation source 130 in the vertical direction, and a drive source that moves the radiation source 130 in the horizontal direction (none of which are shown).

When the imaging posture is the standing position, the electronic cassette 32 is positioned in a predetermined position 49 or the like where it is held in the rack 45. When the imaging posture is the lying position, the electronic cassette 32 is positioned in a predetermined position 51 or the like where it is positioned under an imaging target site on the bed 46.

Although it is not shown in FIG. 2, the console 42 is, in addition to these devices, installed in the radiographic imaging room 44. Further, the electronic cassette 32 is not only used in radiographic imaging rooms or operating rooms but can also be used in medical examinations or rounds inside the hospital, for example, because it is portable.

Figure 3:
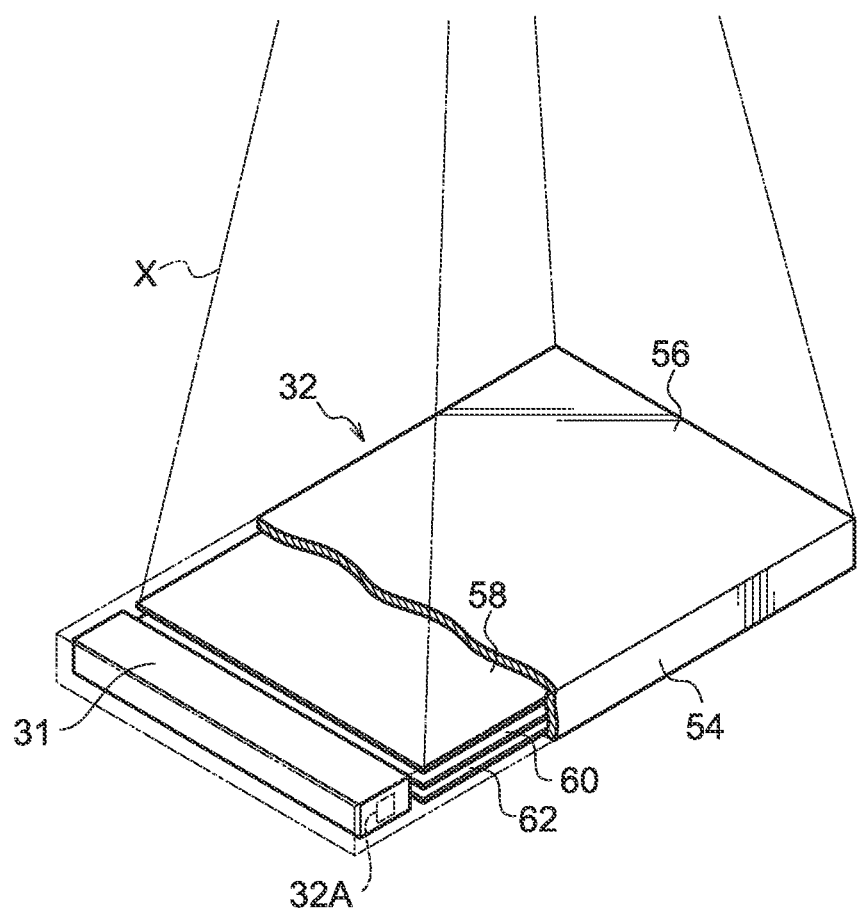
FIG. 3 is a transparent perspective diagram showing the internal configuration of an electronic cassette pertaining to the exemplary embodiment.

FIG. 3 shows the internal configuration of the electronic cassette 32 pertaining to the present exemplary embodiment.

As shown in FIG. 3, the electronic cassette 32 is equipped with a housing 54, which comprises a material that allows the radiation X to pass therethrough, and has a waterproof and airtight structure. When the electronic cassette 32 is used in an operating room or the like, blood or other contaminants may adhere to the electronic cassette 32. Thus, by giving the electronic cassette 32 a waterproof and airtight structure and disinfecting it as needed, the single electronic cassette 32 can be used repeatedly.

Inside the housing 54, a grid 58, the radiation detector 60, and a lead plate 62 are disposed in this order from an irradiated surface 56 side of the housing 54 that is irradiated with the radiation X. The grid 58 removes scattered rays of the radiation X scattered by the patient. The radiation detector 60 detects the radiation X that has passed through the patient. The lead plate 62 absorbs back-scattered rays of the radiation X. The irradiated surface 56 of the housing 54 may also be configured by the grid 58. On a side surface of this housing 54, there is disposed a connection terminal 32A for connecting a cable 43 that includes a built-in communication line 43A and a built-in electrical power line 43B described later.

A case 31 is placed on one end side of the interior of the housing 54. The case 31 houses electronic circuits including a microcomputer and a rechargeable secondary battery. The radiation detector 60 and the electronic circuits are actuated by electrical power supplied from the secondary battery placed in the case 31. It is preferable for a lead plate or the like to be disposed on the irradiated surface 56 side of the case 31 to avoid damage being inflicted on the various circuits housed inside the case 31 in accompaniment with irradiation with the radiation X. The electronic cassette 32 pertaining to the present exemplary embodiment is a cuboid in which the shape of the irradiated surface 56 is rectangular, and the case 31 is placed on one lengthwise direction end portion thereof.

Next, the configurations of relevant portions of the electrical system of the imaging system 18 pertaining to the present exemplary embodiment will be described with reference to FIG. 4.

A connection terminal 34A for communicating with the console 42 is disposed in the radiation generating device 34. A connection terminal 42A for communicating with the radiation generating device 34 and a connection terminal 42B for communicating with the electronic cassette 32 are disposed in the console 42. The connection terminal 34A of the radiation generating device 34 and the connection terminal 42A of the console 42 are interconnected by a cable 35.

When imaging is to be performed, the cable 43 is connected to the connection terminal 32A, whereby the electronic cassette 32 becomes connected to the console 42 via this cable 43.

The radiation detector 60 built into the electronic cassette 32 is configured as a result of a photoelectric conversion layer that absorbs and converts the radiation X into electric charges being layered on a TFT active matrix substrate 66. The photoelectric conversion layer includes, for example, amorphous selenium (a-Se), of which selenium is the main component (e.g., having a content percentage equal to or greater than 50%). When the photoelectric conversion layer is irradiated with the radiation X, the photoelectric conversion layer internally generates electric charges (electron-hole pairs) of an electric charge quantity corresponding to the dose of radiation with which it has been irradiated to thereby convert the radiation X with which it has been irradiated into electric charges. Instead of a material that directly converts the radiation X into electric charges, such as amorphous selenium, the radiation detector 60 may also use a phosphor material and photoelectric conversion elements (photodiodes) to indirectly convert the radiation X into electric charges. Examples of phosphor materials include gadolinium oxysulfide (GOS) and cesium iodide (CsI), which are well known. In this case, the phosphor material converts the radiation X into light, and the photoelectric conversion element photodiodes convert the light into electric charges.

Numerous pixel portions 74 equipped with storage capacitors 68 and TFTs 70 (in FIG. 4, the photoelectric conversion layer corresponding to the individual pixel portions 74 is schematically shown as photoelectric conversion portions 72) are arranged in a matrix on the TFT active matrix substrate 66. The storage capacitors 68 store the electric charges that have been generated by the photoelectric conversion layer. The TFTs 70 are for reading out the electric charges that have been stored in the storage capacitors 68. The electric charges that have been generated in the photoelectric conversion layer in accompaniment with irradiation of the electronic cassette 32 with the radiation X are stored in the storage capacitors 68 of the individual pixel portions 74. Therefore, image data that had been carried in the radiation X with which the electronic cassette 32 was irradiated is converted into electric charge and is held in the radiation detector 60.

Plural gates lines 76 and plural data lines 78 are disposed on the TFT active matrix substrate 66. The plural gate lines 76 extend in a certain direction (row direction) and are for switching on and off the TFTs 70 of the individual pixel portions 74. The plural data lines 78 extend in a direction (column direction) orthogonal to the gate lines 76 and are for reading out the stored electric charges from the storage capacitors 68 via the TFTs 70 that have been switched on. The individual gate lines 76 are connected to a gate line driver 80, and the individual data lines 78 are attached to a signal processor 82. When electric charges are stored in the storage capacitors 68 of the individual pixel portions 74, the TFTs 70 of the individual pixel portions 74 are switched on in order in row units by signals supplied via the gate lines 76 from the gate line driver 80. The electric charges being stored in the storage capacitors 68 of the pixel portions 74 whose TFTs 70 have been switched on are transmitted through the data lines 78 as analog electrical signals and are inputted to the signal processor 82. Consequently, the electric charges being stored in the storage capacitors 68 of the individual pixel portions 74 are read out in order in row units.

Figure 5:
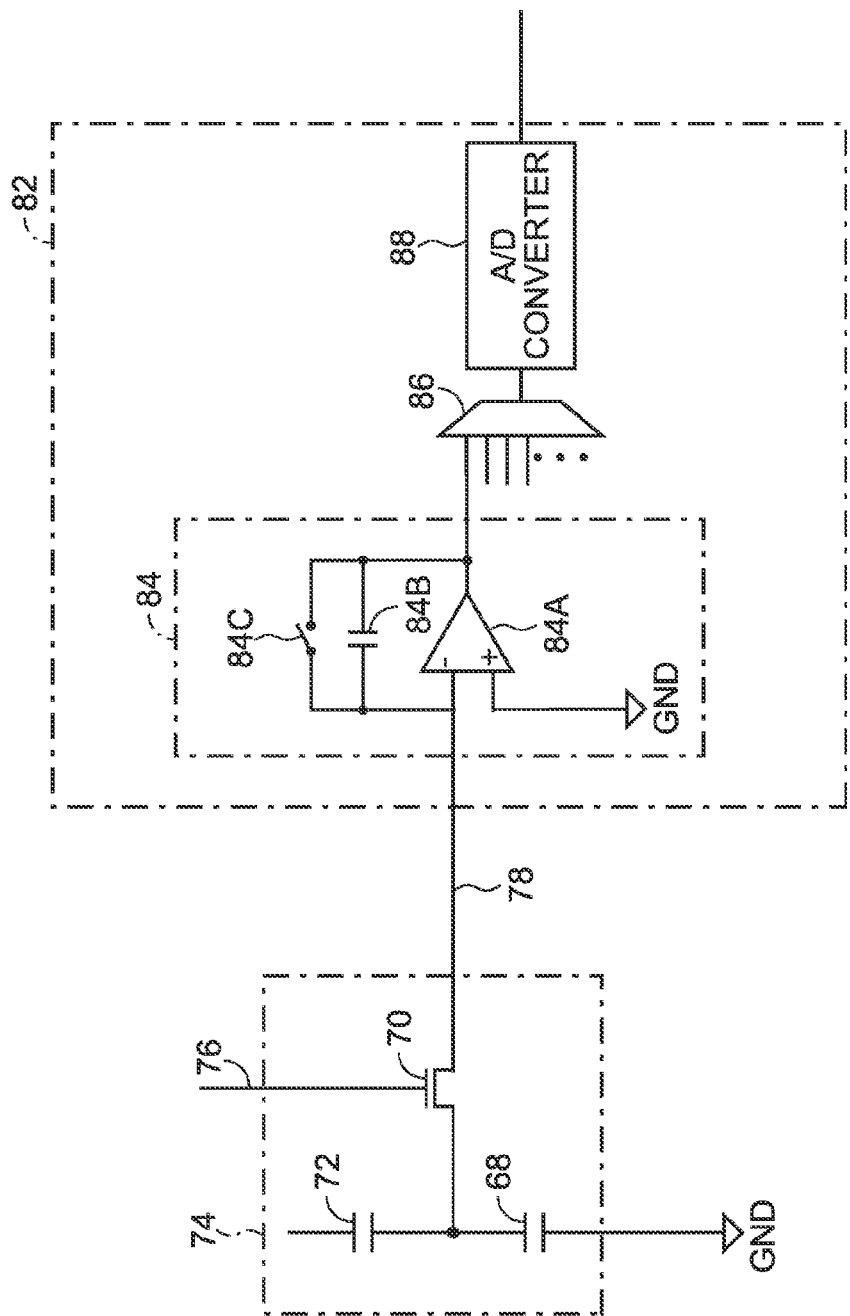
FIG. 5 is an equivalent circuit diagram focusing on one pixel portion of a radiation detector pertaining to the exemplary embodiment.

FIG. 5 shows an equivalent circuit diagram focusing on one pixel portion of the radiation detector 60 pertaining to the present exemplary embodiment.

As shown in FIG. 5, the source of the TFT 70 is connected to the data line 78, and the data line 78 is connected to the signal processor 82. The drain of the TFT 70 is connected to the storage capacitor 68 and to the photoelectric converter 72, and the gate of the TFT 70 is connected to the gate line 76.

The signal processor 82 is equipped with a sample-and-hold circuit 84 for each of the individual data lines 78. The electric charge signals that have been transmitted through the individual data lines 78 are held in the sample-and-hold circuits 84. The sample-and-hold circuit 84 is configured to include an op-amp 84A and a capacitor 84B and converts the electric charge signal into an analog voltage. The sample-and-hold circuit 84 is also disposed with a switch 84C, which serves as a reset circuit that causes both electrodes of the capacitor 84B to short to cause the electric charge stored in the capacitor 84B to be discharged. The gain of the op-amp 84 can be adjusted by control from a cassette controller 92 described later.

A multiplexer 86 and an analog-to-digital (A/D) converter 88 are connected in this order to output sides of the sample-and-hold circuits 84. The electric charge signals held in the individual sample-and-hold circuits 84 are converted into analog voltages, and the analog voltages are inputted in order (serially) to the multiplexer 86 and converted into digital image data by the A/D converter 88.

Figure 4:
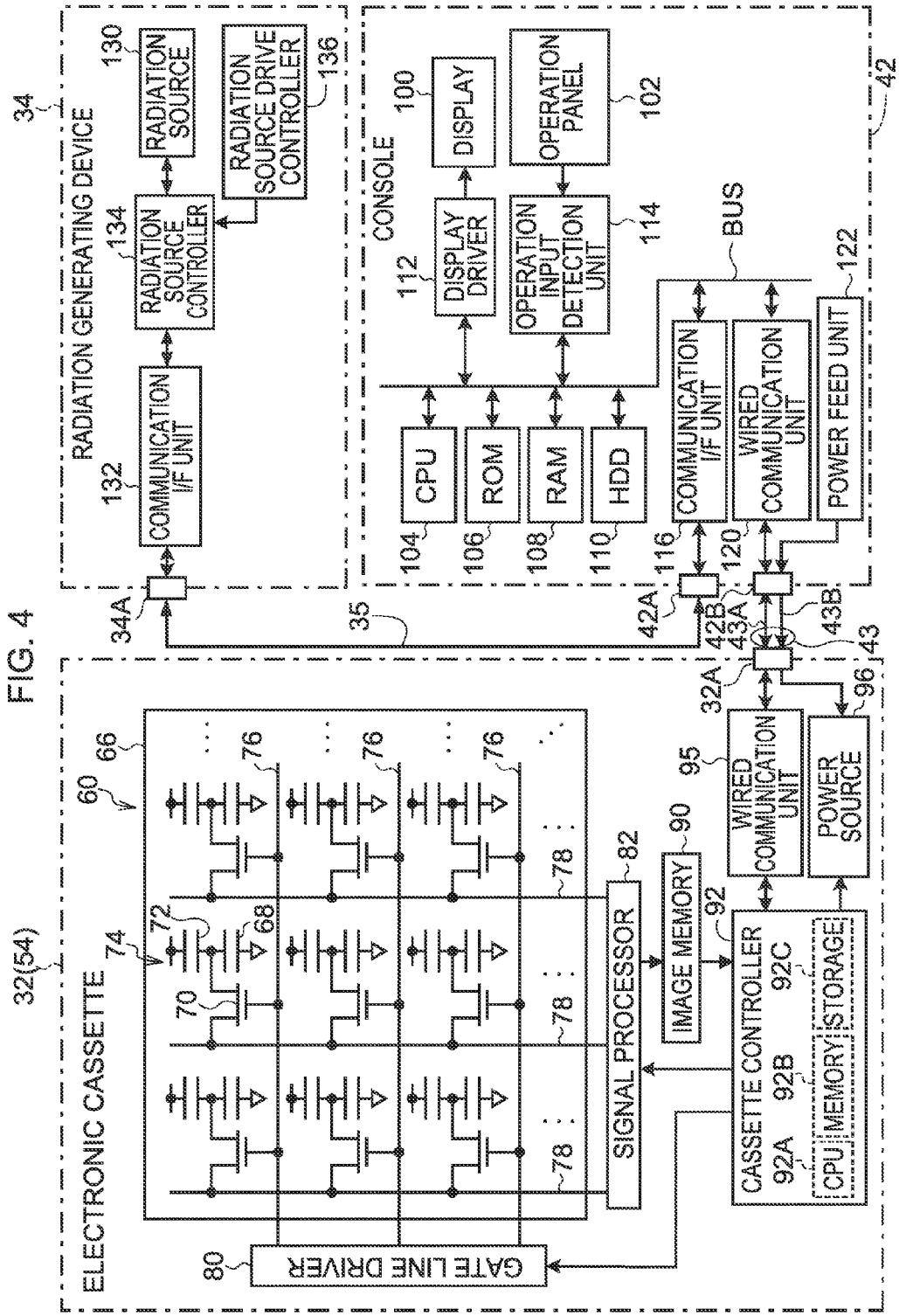
FIG. 4 is a block diagram showing the detailed configuration of the radiographic image capturing system pertaining to the exemplary embodiment.

An image memory 90 is connected to the signal processor 82 (see FIG. 4). The image data outputted from the A/D converter 88 of the signal processor 82 are stored in order in the image memory 90. The image memory 90 has a storage capacity capable of storing plural frames of image data. Each time a radiographic image is captured, the image data obtained by the imaging are sequentially stored in the image memory 90.

The image memory 90 is connected to a cassette controller 92 that controls the operation of the entire electronic cassette 32. The cassette controller 92 is configured by a microcomputer and is equipped with a central processing unit (CPU) 92A, a memory 92B including a read-only memory (ROM) and a random access memory (RAM), and a nonvolatile storage 92C comprising a hard disk drive (HDD) or a flash memory.

A wired communication unit 95 is connected to the cassette controller 92. The wired communication unit 95 is connected to the connection terminal 32A and controls the transmission of various types of data between the electronic cassette 32 and the console 42 via the connection terminal 32A and the communication line 43A of the cable 43. The cassette controller 92 can communicate with the console 42 via the wired communication unit 95 and transmits and receives various types of data to and from the console 42. The cassette controller 92 stores later-described exposure conditions received via the wired communication unit 95 from the console 42 and initiates read-out of the electric charges on the basis of the exposure conditions.

A power source 96 is disposed in the electronic cassette 32. Electrical power is supplied to the power source 96 from the electrical power line 43B of the cable 43 connected to the connection terminal 32A. The various circuits and elements mentioned above (the gate line driver 80, the signal processor 82, the image memory 90, the wired communication unit 95, the microcomputer functioning as the cassette controller 92, etc.) are actuated by electrical power supplied from the power source 96. The power source 96 has the aforementioned built-in battery (secondary battery) so as to not impede the portability of the electronic cassette 32, and the power source 96 charges the battery with the electrical power supplied via the cable 43 and supplies electrical power to the various circuits and elements. FIG. 4 does not show lines connecting the various circuits and elements to the power source 96.

The cassette controller 92 is connected to the power source 96, outputs a power source control signal, and controls the charging of the power source 96 with the electrical power from the console 43.

Figure 6:
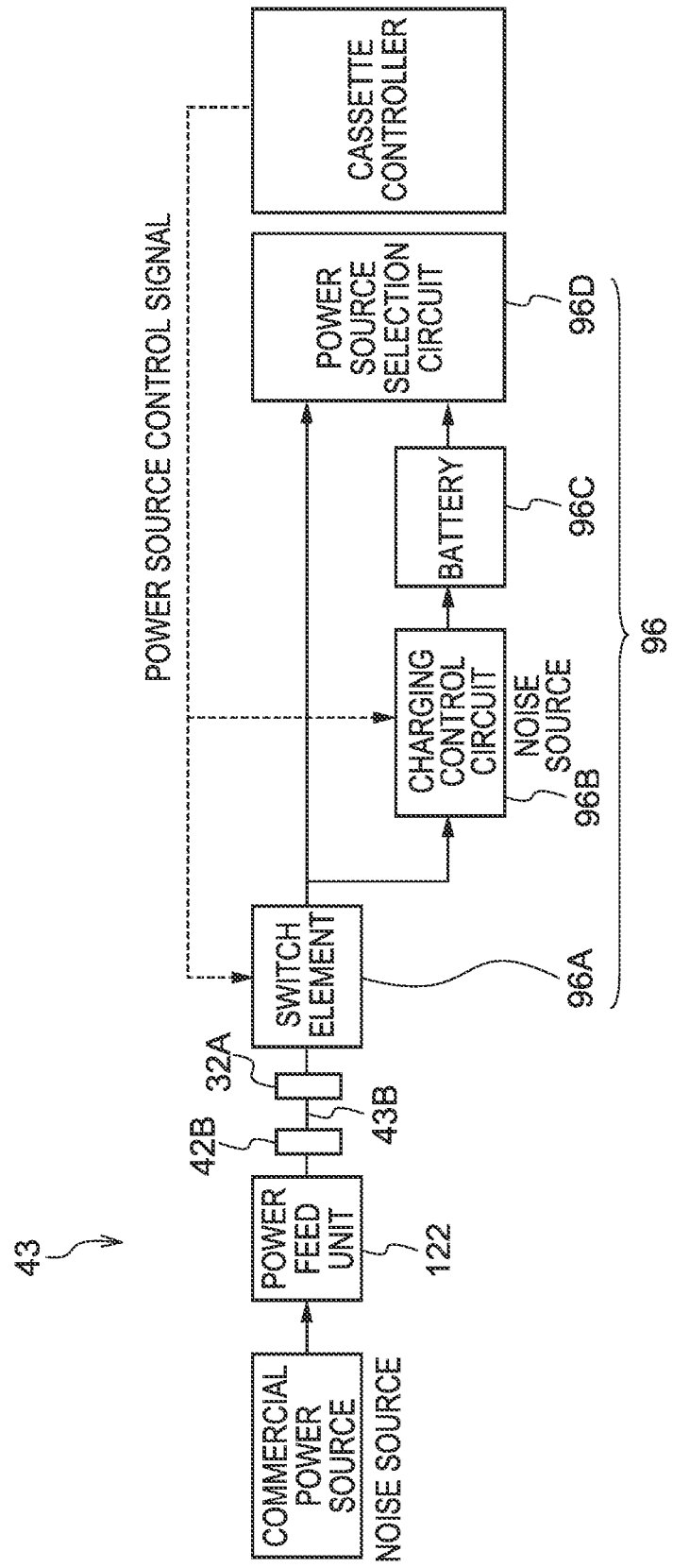
FIG. 6 is a block diagram showing the detailed configuration of a power source pertaining to the exemplary embodiment.

FIG. 6 shows the detailed configuration of the power source 96 of the electronic cassette 32 pertaining to the present exemplary embodiment.

Electrical power is supplied from the console 43 to the electrical power line 43B. The electrical power is supplied to the power source 96 as a result of the cable 43 being connected to the connection terminal 32A.

The power source 96 is equipped with a switch element 96A, a charging control circuit 96B, a battery 96C, and a power source selection circuit 96D.

One end side of the switch element 96A is connected to the connection terminal 32A, and the other end side of the switch element 96A branches and is connected to the power source selection circuit 96D and to the charging control circuit 96B. The switch element 96A can shut off the electrical power supplied via the connection terminal 32A from the electrical power line 43B as a result of being switched on and off in response to the power source control signal from the cassette controller 92.

The charging control circuit 96B is connected to the switch element 96A and to the battery 96C and controls the charging of the battery 96C. The charging control circuit 96B is configured to include a DC-DC converter, for example, and charges the battery 96C by transforming the electrical power supplied via the switch element 96A into a voltage suited for charging the battery 96C and supplying that voltage to the battery 96C. Further, the charging control circuit 96B has a built-in protection circuit for preventing overcharging and over-discharging of the battery 96C. Therefore, in a case where the battery 96C may be overcharged, the protection circuit shuts off the supply of electrical power to the battery 96C, and in a case where the battery 96C may be over-discharged, the protection circuit stops discharge from the battery 96C. Moreover, the charging control circuit 96B can stop the operation of charging the battery 96C in response to the power source control signal from the cassette controller 92.

The power source selection circuit 96D is connected to the switch element 96A and to the battery 96C and monitors the electrical power supplied from the switch element 96A. In a case where electrical power from the switch element 96A is being supplied, the power source selection circuit 96D selects and outputs the electrical power from the switch element 96A, and in a case where the supply of electrical power from the switch element 96A has stopped, the power source selection circuit 96D selects and outputs the electrical power from the battery 96C.

The console 42 (see FIG. 4) is configured as a server computer. The console 42 is equipped with a display 100, which displays operation menus, captured radiographic images, and so forth, and an operation panel 102, which is configured to include plural keys and to which various types of data and operation instructions are inputted.

The console 42 pertaining to the present exemplary embodiment is also equipped with a CPU 104 that controls the operation of the entire device, a ROM 106 in which various programs including a control program are stored beforehand, a RAM 108 that temporarily stores various types of data, a HDD 110 that stores and holds various types of data, a display driver 112 that controls the display of various types of data on the display 100, and an operation input detection unit 114 that detects states of operation with respect to the operation panel 102. The console 42 is also equipped with a communication I/F unit 116 and a wired communication unit 120. The communication I/F unit 116 is connected to the connection terminal 42A and transmits and receives various types of data such as later-described exposure conditions to and from the radiation generating device 34 via the connection terminal 42A and the cable 35. The wired communication unit 120 is connected to the connection terminal 42B and transmits and receives various types of data such as image data to and from the electronic cassette 32 via the connection terminal 42B and the cable 43.

The CPU 104, the ROM 106, the RAM 108, the HDD 110, the display driver 112, the operation input detection unit 114, the communication I/F unit 116, and the wired communication unit 120 are interconnected via a system bus BUS. Consequently, the CPU 104 can access the ROM 106, the RAM 108, and the HDD 110 and can control the display of various types of data on the display 100 via the display driver 112, control the transmission and reception of various types of data to and from the radiation generating device 34 via the communication I/F unit 116, and control the transmission and reception of various types of data to and from the electronic cassette 32 via the wired communication unit 120. The CPU 104 can also grasp, via the operation input detection unit 114, states of operation by a user with respect to the operation panel 102.

The console 42 pertaining to the present exemplary embodiment is also equipped with a power feed unit 122 that supplies electrical power to the electronic cassette 32 via the connection terminal 42B and the cable 43. The console 42 supplies the electrical power to the electronic cassette 32 via the electrical power line 43B of the cable 43.

The radiation generating device 34 is equipped with the radiation source 130 that outputs the radiation X, a communication I/F unit 132, a radiation source controller 134, and a radiation source drive controller 136. The communication I/F unit 132 transmits and receives various types of data, such as the exposure conditions, posture information, and state information of the radiation generating device 34, to and from the console 42. The radiation source controller 134 controls the radiation source 130 on the basis of the received exposure conditions. The radiation source drive controller 136 controls the operation of the supporting-and-moving mechanism 52 by controlling the supply of electrical power to each of the drive sources with which the supporting-and-moving mechanism 52 is equipped.

The radiation source controller 134 is also realized by a microcomputer and stores the received exposure conditions and posture information. The exposure conditions received from the console 42 include information such as tube voltage, tube current, and the duration of irradiation. The posture information includes information indicating whether the imaging posture is the standing position or the lying position. When the imaging posture designated by the received posture information is the standing position, the radiation source controller 134 controls the supporting-and-moving mechanism 52 via the radiation source drive controller 136 such that the radiation source 130 is positioned in a position 53A for standing position imaging (see FIG. 2; this is a position where the patient positioned in the imaging position 48 is irradiated from the side with the emitted radiation). When the imaging posture designated by the received posture information is the lying position, the radiation source controller 134 controls the supporting-and-moving mechanism 52 via the radiation source drive controller 136 such that the radiation source 130 is positioned in a position 53B for lying position imaging (see FIG. 2; this is a position where the patient positioned in the imaging position 50 is irradiated from above with the emitted radiation). Then, the radiation source controller 134 causes the radiation source 130 to irradiate the patient with the radiation X on the basis of the received exposure conditions.

Next, the action of the imaging system 18 pertaining to the present exemplary embodiment will be described.

The imaging system 18 pertaining to the present exemplary embodiment is configured such that its imaging mode can be selected between still-image imaging, in which imaging is performed once at a time, and fluoroscopy, in which imaging is performed continuously.

Any of the terminal devices 12 (see FIG. 1) receives an imaging request from a doctor or a radiologic technologist in a case where a radiographic image is to be captured. In the imaging request, the patient to be imaged, the site to be imaged, and the imaging mode are designated, and tube voltage, tube current, the duration of irradiation, and the dose of radiation with which the patient is to be irradiated are designated as needed.

The terminal device 12 notifies the RIS server 14 of the content of the imaging request it has received. The RIS server 14 stores in the database 14A the content of the imaging request of which it has been notified by the terminal device 12.

The console 42 acquires the content of the imaging request and the attribute information of the patient to be imaged from the RIS server 14 by accessing the RIS server 14 and displays the content of the imaging request and the attribute information of the patient on the display 100 (see FIG. 4).

The person responsible for imaging initiates capture of the radiographic image on the basis of the content of the imaging request displayed on the display 100.

For example, as shown in FIG. 2, when an affected area of an examinee lying on the bed 46 is to be imaged, the person responsible for imaging interconnects the electronic cassette 32 and the console 42 with the cable 43 and then places the electronic cassette 32 between the bed 46 and the affected area of the examinee depending on the site of imaging.

Then, the person responsible for imaging designates, with respect to the operation panel 102, still-image imaging or fluoroscopy as the imaging mode. In a case where still-image imaging has been designated as the imaging mode, the person responsible for imaging also designates, with respect to the operation panel 102, exposure conditions such as tube voltage, tube current, and the duration of irradiation when irradiating the examinee with the radiation X. In a case where fluoroscopy has been designated as the imaging mode, the person responsible for imaging also designates, with respect to the operation panel 102, exposure conditions such as frame rate, tube voltage, and tube current.

When the exposure condition designation operation is performed with respect to the operation panel 102, in a case where fluoroscopy has been designated, the console 42 obtains the duration of irradiation corresponding to the designated frame rate and transmits to the radiation generating device 34 via the communication cable 35 the exposure conditions, such as tube voltage, tube current, and the duration of irradiation, and the posture information. The console 42 also transmits to the electronic cassette 32 imaging control information such as the storage time in which the electric charges are to be stored in each of the storage capacitors 68 of the radiation detector 60 when capturing a radiographic image.

When preparation for imaging in the radiation generating device 34 is completed, the person responsible for imaging performs, with respect to the operation panel 102 of the console 42, an imaging instruction operation instructing imaging. When the imaging instruction operation is performed with respect to the operation panel 102, the console 42 transmits instruction instructing the start of exposure to the radiation generating device 34 and the electronic cassette 32. Therefore, the radiation source 130 generates and emits the radiation at the tube voltage, the tube current, and the duration of irradiation corresponding to the exposure conditions that the radiation generating device 34 received from the console 42.

Figure 7:
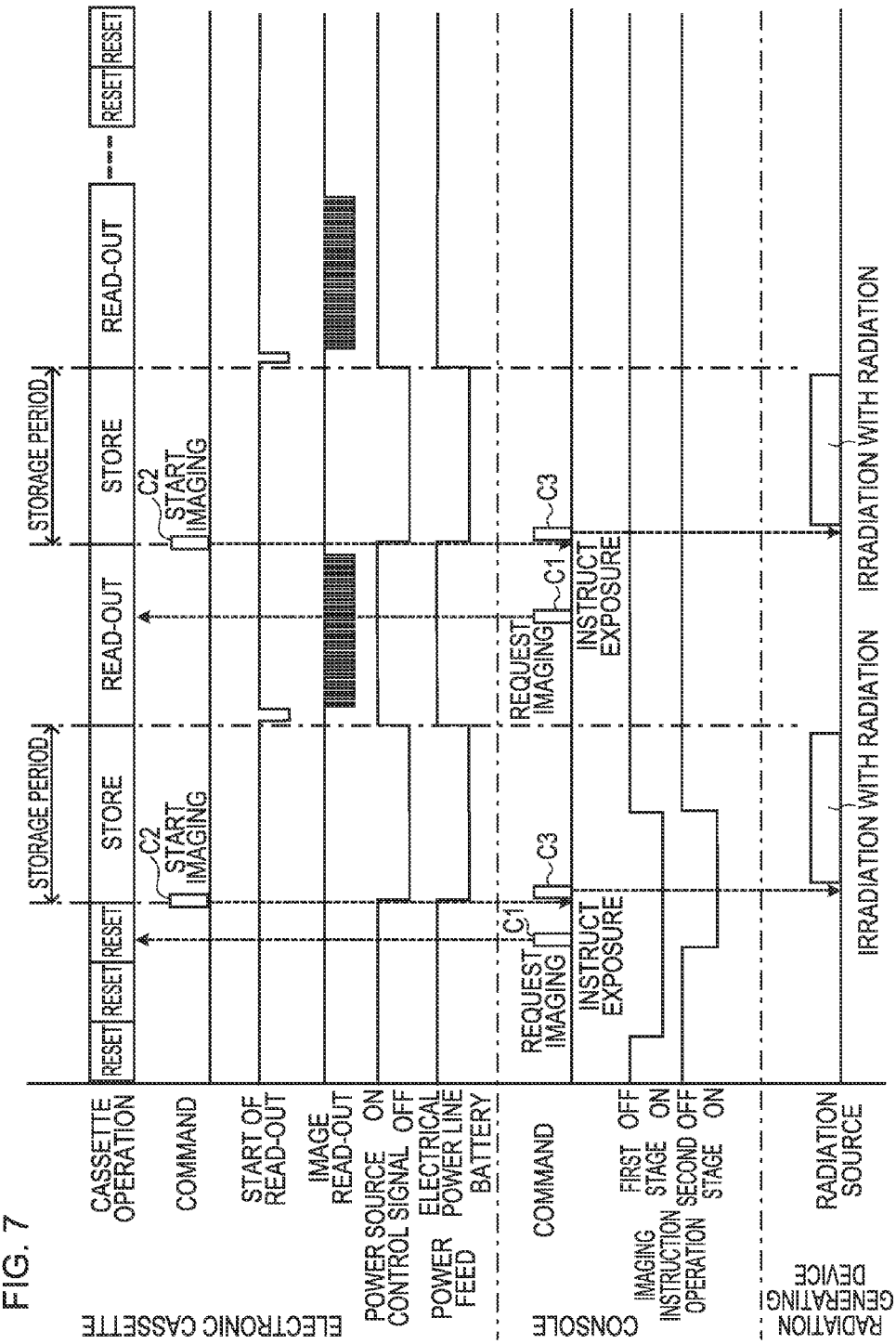
FIG. 7 is a timing chart showing a flow of operation when capturing a radiographic image pertaining to the exemplary embodiment.

FIG. 7 shows a time chart showing a flow of an imaging operation in a case where fluoroscopy is performed.

In the radiation detector 60 built into the electronic cassette 32, in a case where the power source of the electronic cassette 32 is in an ON state, electric charges are stored in each of the storage capacitors 68 because of dark current or the like even in a state where the radiation detector 60 is not being irradiated with the radiation X. For this reason, in the case of a state of preparation for imaging, the cassette controller 92 controls the gate line driver 80 so as to cause an ON signal to be outputted from the gate line driver 80 to each of the gate lines 76 in order one line at a time and switch on, in order one line at a line, each of the TFTs 70 connected to each of the gate lines 76. Therefore, the electric charges stored in each of the storage capacitors 68 in order one line at a time flow out to each of the data lines 78 as electric charge signals. During the state of preparation for imaging, the cassette controller 92 repeats a reset operation in which it causes an ON signal to be outputted to each of the gate lines 76 in order one line at a time and resets, equal to one frame, the electric charges stored in each of the storage capacitors 68.

When preparation for imaging in the radiation generating device 34 is completed, the person responsible for imaging performs, with respect to the operation panel 102 of the console 42, an imaging instruction operation instructing imaging. In the imaging system 18 pertaining to the present exemplary embodiment, the imaging instruction operation with respect to the operation panel 102 is configured as an operation in two stages, so that capture of a radiographic image is performed when an imaging instruction operation of a second stage is performed after an imaging instruction operation of a first stage with respect to the operation panel 102. This two-stage imaging instruction operation may, for example, be performed by pressing two buttons on the operation panel 102 in order, or may, for example, be performed by first half-pressing and then fully-pressing a single button.

When the imaging instruction operation of the second stage is performed with respect to the operation panel 102, the console 42 transmits to the electronic cassette 32 instruction C1 requesting imaging.

When the instruction C1 requesting imaging is received, the cassette controller 92 performs the reset operation until a reset operation equal to one frame is completed and, after the completion of the reset operation equal to one frame, transmits to the console 42 instruction C2 instructing the start of imaging.

When the console 42 receives the instruction C2 instructing the start of imaging, the console 42 transmits to the radiation generating device 34 via the communication cable 35 instruction C3 instructing exposure. When the instruction C3 instructing exposure is received, the radiation generating device 34 causes the radiation source 130 to irradiate the patient with the radiation X for the duration of irradiation described by the exposure condition information that was stored immediately before.

The radiation X emitted from the radiation source 130 passes through the patient and then reaches the electronic cassette 32. Therefore, electric charges corresponding to the dose of the radiation X with which the patient has been irradiated are stored in the storage capacitors 68 of each of the pixel portions 74 of the radiation detector 60 built into the electronic cassette 32.

After transmitting the instruction C2 instructing the start of imaging, the cassette controller 92 stands by for a storage time determined in the imaging control information, then controls the gate line driver 80 so as to cause an ON signal to be outputted from the gate line driver 80 to each of the gate lines 76 in order one line at a time and switch on, in order one line at a time, each of the TFTs 70 connected to each of the gate lines 76.

In the radiation detector 60, when each of the TFTs 70 connected to each of the gate lines 76 is switched on in order one line at a time, the electric charges stored in each of the storage capacitors 68 in order one line at a time flow out to each of the data lines 78 as electric charge signals. The electric charge signals flowing out to each of the data lines 78 are inputted to the individual sample-and-hold circuits 84 and are converted into voltage signals. Then, the converted voltage signals are inputted in order (serially) to the multiplexer 86 and are converted into digital image data. Then, the digital image data is stored in the memory 90.

When read-out of image data equal to one frame (equal to one image) ends, the cassette controller 92 transmits the image data stored in the memory 90 to the console 42 one frame at a time.

The console 42 again transmits to the electronic cassette 32 the instruction C1 requesting imaging in order to perform the next imaging in an imaging cycle corresponding to the designated frame rate.

When the instruction C1 requesting imaging is received, the cassette controller 92 transmits to the console 42 instruction C2 instructing the start of imaging after the end of read-out of an image equal to one frame.

The imaging system 18 pertaining to the present exemplary embodiment captures a video by repeatedly performing this operation.

Various types of corrective image processing such as shading compensation are performed in the console 42 on the image that has been transmitted to the console 42, and the image is stored in the HDD 110. The image data stored in the HDD 110 is displayed on the display 100 to check the captured radiographic image and so forth, is transferred to the RIS server 14, and is also stored in the database 14A.

When an imaging end operation is performed with respect to the operation panel 102, capture of a video ends when the console 42 stops transmitting the instruction C1 requesting imaging.

Incidentally, there are cases where noise is included in electrical power supplied from commercial power sources, and there are cases where that noise is transmitted via the electrical power line 43B and ends up riding on the image data. Further, in the charging control circuit 96B, noise occurs when the supplied electrical power is transformed into a voltage suited for charging the battery 96C, and there are cases where that noise ends up riding on the image data. Particularly when noise occurs in a storage period, the influence on the image data is large.

Thus, in storage periods in which the radiation detector 60 stores electric charges, the electronic cassette 32 shuts off the electrical power supplied via the connection terminal 32A to thereby shut off supply of electrical power to the battery 96C. Specifically, as shown in FIG. 7, the cassette controller 92 uses the instruction C2 instructing the start of imaging as a trigger to output the power source control signal instructing off with respect to the switch element 96A and the charging control circuit 96B to thereby shut off the electrical power supplied via the electrical power line 43B and stop the operation of charging the battery 96C from the point in time when the cassette controller 92 transmits the instruction C2 to the console 42 to until the storage time determined by the imaging control information elapses. In the case where the electrical power supplied via the connection terminal 32A has been shut off, the power source selection circuit 96D outputs the electrical power with which the battery 96C has been charged because the electrical power from the battery 96C is outputted.

Therefore, according to the present exemplary embodiment, in the storage period of each imaging, supply of electrical power via the electrical power line 43B is shut off and the electronic cassette 32 becomes driven by electrical power from the battery 96C, so the effect of noise transmitted from an outside power source on radiographic images is suppressed. Further, in periods between the storage times of each imaging, supply of electrical power via the electrical power line 43B is performed and the battery 96C becomes charged with that electrical power, so prolonged capture of a video can be performed.

While the present invention has been described above using an exemplary embodiment, the technical scope of the present invention is not limited to the scope described in the above exemplary embodiment. Various changes or improvements can be made to the above exemplary embodiment in a scope not departing from the gist of the invention, and the technical scope of the present invention also includes embodiments to which such changes or improvements are made.

Further, the above exemplary embodiment is not intended to limit the inventions pertaining to the claims, and not all combinations of features described in the exemplary embodiment are necessarily essential to the solving means of the invention. The exemplary embodiment includes inventions in various stages, and various inventions can be extracted by appropriate combinations of the plural configuration requirements disclosed. Even when several configuration requirements are omitted from all the configuration requirements disclosed in the exemplary embodiment, configurations from which those several configuration requirements are omitted can also be extracted as inventions as long as effects are obtained.

Further, in the above embodiment, a case has been described where the supply of electrical power from the electrical power line 43B and the operation of charging the battery 96C are both stopped, but the present invention is not limited to this and may also be configured such that only either one is performed.

Further, in the above embodiment, a case has been described where, in the case of the state of preparation for imaging, the electronic cassette 32 repeats the reset operation, and when the instruction C1 requesting imaging is received, the electronic cassette 32 performs the reset operation until a reset operation equal to one frame is completed, and after the completion of the reset operation equal to one frame, the electronic cassette 32 transmits to the console 42 the instruction C2 instructing the start of imaging and starts storing the electric charges, but the present invention is not limited to this. Further, a case has been described where the electronic cassette 32 uses the instruction C2 instructing the start of imaging as a trigger to output the power source control signal instructing off with respect to the switch element 96A and the charging control circuit 96B, but the present invention is not limited to this.

Further, in the above embodiment, a case has been described where the electronic cassette 32 and the console 42 communicate with each other via the communication cable 43, but the present invention is not limited to this and may also be configured such that the electronic cassette 32 and the console 42 communicate with each other wirelessly.

Further, in the above embodiment, a case has been described where the electronic cassette 32 is supplied with electrical power from the console 42, but the present invention is not limited to this and may also be configured such that the electronic cassette 32 is supplied with electrical power directly from a commercial power source.

In addition, the configuration of the RIS 10 (see FIG. 1), the configurations of the radiographic imaging room and the radiation generating device 34 (see FIG. 2), the configuration of the electronic cassette 32 (see FIG. 3), and the configuration of the imaging system 18 (see FIG. 4) described in the above exemplary embodiment are examples, and it goes without saying that unwanted portions can be omitted, new portions can be added, and states of connection and so forth can be changed in a scope not departing from the gist of the present invention.

According to the above exemplary embodiment, the radiation detector has the plural sensor portions in which electric charges are generated as a result of being irradiated with radiation and which store the generated electric charges. The detection circuit reads out, as electrical signals, electric charge quantities stored in each of the sensor portions of the radiation detector, converts the electrical signals it has read into digital data, and detects image data representing a radiographic image.

Further, the receiver receives electrical power supplied from the outside. The power source is charged by the electrical power received by the receiver, and electrical power for driving is supplied by the power source to at least the radiation detector and the detection circuit.

Additionally, in the case of performing video imaging in which imaging is performed continuously, the controller controls the detection circuit so as to allow electric charges to be stored in a predetermined storage period in each of the sensor portions of the radiation detector in each imaging and thereafter read out stored electric charges. The controller also performs control such that, in the storage period of each imaging, it stops at least one of the charging of the power source with the electrical power received by the receiver and the reception of the electrical power from the outside by the receiver and such that, in periods between the storage period of each imaging, it charges the power source with the electrical power received by the receiver.

In this manner, according to the above exemplary embodiment, in the case of performing video imaging in which imaging is performed continuously, electric charges are allowed to be stored in the predetermined storage period in each of the sensor portions of the radiation detector in each imaging and thereafter the stored electric charges are read out, and, in the storage period of each imaging, at least one of the charging of the power source with the electrical power from the outside and the reception of the electrical power from the outside is stopped, and, in the periods between the storage period of each imaging, the power source is charged with the electrical power received from the outside. Therefore, prolonged capture of a video can be performed while suppressing the effect of noise transmitted from the outside power source on radiographic images.

In the present invention, in the case of a state of preparation for imaging, the controller may also perform control so as to repeatedly perform a reset operation that retrieves the electric charges stored in each of the sensor portions of the radiation detector, and, when performing imaging, the controller may also perform control so as to perform the reset operation until a reset operation equal to one frame is completed and, after completion of the reset operation equal to one frame, causes storage of the electric charges in the storage period to be started in each of the sensor portions of the radiation detector and stops at least one of the charging of the power source with the electrical power received by the receiver or the reception of electrical power from the outside by the receiver.

According to the present invention, there is obtained the effect that prolonged capture of a video can be performed while suppressing the effect of noise transmitted from the outside power source on radiographic images.

What is claimed is:

1. A radiographic image capturing device comprising:
    a radiation detector that has a plurality of sensor portions in which electric charges are generated as a result of being irradiated with radiation and which store the generated electric charges;
    a detection circuit that reads out, as electrical signals, electric charge quantities stored in each of the sensor portions of the radiation detector, converts the electrical signals it has read out into digital data, and detects image data representing a radiographic image;
    a receiver that receives external electrical power;
    a power source that is charged by the electrical power received by the receiver and that supplies electrical power for driving at least the radiation detector and the detection circuit; and
    a controller which, in the case of performing video imaging in which imaging is performed continuously, controls the detection circuit so as to allow electric charges to be stored in a predetermined storage period in each of the sensor portions of the radiation detector in each imaging and thereafter to read out the stored electric charges, and which performs control such that, in the storage period of each imaging, the controller stops at least one of the charging of the power source with the electrical power received by the receiver or the reception of the electrical power from the outside by the receiver, and performs control such that, in periods between the storage period of each imaging, the controller charges the power source with the electrical power received by the receiver.

2. The radiographic image capturing device according to claim 1, wherein in the case of a state of preparation for imaging, the controller performs control so as to repeatedly perform a reset operation that retrieves the electric charges stored in each of the sensor portions of the radiation detector, and, when performing imaging, the controller performs control so as to perform the reset operation until a reset operation equal to one frame is completed.

3. The radiographic image capturing device according to claim 2, wherein the controller, after completion of the reset operation equal to one frame, causes storage of the electric charges in the storage period to be started in each of the sensor portions of the radiation detector and stops at least one of the charging of the power source with the electrical power received by the receiver or the reception of electrical power from the outside by the receiver.

4. The radiographic image capturing device according to claim 2, wherein the controller communicates with an external console that is connected to a radiation source, and performs control so as to begin the reset operation when receiving an instruction from the console indicating that a request for imaging has been received.

5. The radiographic image capturing device according to claim 4, wherein the controller sends an instruction to the console to begin radiation after completion of the reset operation equal to one frame, and thereafter performs control so as to stop at least one of the charging of the power source with the electrical power received by the receiver or the reception of electrical power from the outside by the receiver.

* * * * *